United States Patent
Steffier et al.

(10) Patent No.: US 9,107,857 B2
(45) Date of Patent: *Aug. 18, 2015

(54) METHOD AND COMPOSITION FOR REMOVING RADIATION-CURABLE, PIGMENTED, ARTIFICIAL NAIL GEL COATINGS

(71) Applicant: MYCONE Dental Supply Co., Inc., Cherry Hill, NJ (US)

(72) Inventors: Lawrence W Steffier, Cherry Hill, NJ (US); Kevin Sheran, Philadelphia, PA (US); Michael Hurt, Danville, PA (US); Gary Iannece, Bordentown, NJ (US)

(73) Assignee: Mycone Dental Supply Co., Inc., Cherry Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/217,799

(22) Filed: Mar. 18, 2014

(65) Prior Publication Data

US 2014/0221264 A1    Aug. 7, 2014

Related U.S. Application Data

(62) Division of application No. 13/434,408, filed on Mar. 29, 2012, now Pat. No. 8,697,619.

(60) Provisional application No. 61/468,909, filed on Mar. 29, 2011.

(51) Int. Cl.
| | | |
|---|---|---|
| *C11D 7/22* | (2006.01) | |
| *C11D 7/26* | (2006.01) | |
| *C11D 7/50* | (2006.01) | |
| *B08B 3/04* | (2006.01) | |
| *A61K 8/92* | (2006.01) | |
| *A61Q 3/04* | (2006.01) | |

(52) U.S. Cl.
CPC . *A61K 8/925* (2013.01); *A61Q 3/04* (2013.01); *B08B 3/04* (2013.01); *C11D 7/263* (2013.01); *C11D 7/264* (2013.01)

(58) Field of Classification Search
CPC .......... C11D 7/263; C11D 7/264; C11D 7/46; B08B 3/04
USPC ............... 510/118, 201, 505, 506; 134/38
See application file for complete search history.

(56) References Cited

U.S. PATENT DOCUMENTS

| | | | |
|---|---|---|---|
| 4,197,212 A | 4/1980 | Minton et al. | |
| 4,682,612 A | 7/1987 | Giuliano | |
| 4,824,662 A | 4/1989 | Hofmann | |
| 5,024,779 A | 6/1991 | Helioff et al. | |
| 5,077,038 A | 12/1991 | Hofmann | |
| 5,173,288 A | 12/1992 | Everhart et al. | |
| 5,342,536 A | 8/1994 | Miner et al. | |
| 5,486,305 A | 1/1996 | Faryniarz et al. | |
| 7,276,476 B2 | 10/2007 | Chang et al. | |
| 8,697,619 B2* | 4/2014 | Steffier et al. | 510/118 |
| 2002/0010226 A1* | 1/2002 | Lilley | 522/14 |
| 2003/0073753 A1* | 4/2003 | Lilley et al. | 522/18 |
| 2005/0065297 A1* | 3/2005 | Patel | 525/532 |
| 2005/0202982 A1 | 9/2005 | Perlman | |
| 2007/0015692 A1 | 1/2007 | Chang et al. | |
| 2008/0159973 A1* | 7/2008 | Doan | 424/61 |
| 2010/0317595 A1 | 12/2010 | Mullins | |
| 2011/0182837 A1* | 7/2011 | Steffier | 424/61 |
| 2011/0226271 A1* | 9/2011 | Raney et al. | 132/200 |
| 2011/0256080 A1* | 10/2011 | Kozachek et al. | 424/61 |
| 2012/0199151 A1* | 8/2012 | Haile | 132/200 |
| 2012/0252710 A1 | 10/2012 | Steffier et al. | |
| 2013/0199559 A1* | 8/2013 | Haile | 132/200 |

OTHER PUBLICATIONS

Rita-General Product Listing, International Division, pp. 1-21, Feb. 2005.

\* cited by examiner

*Primary Examiner* — Gregory R Delcotto

(74) *Attorney, Agent, or Firm* — Michael B. Fein; Eckert Seamans Cherin & Mellott, LLC

(57) ABSTRACT

A method and composition for removing UV cured nail gel wherein the composition comprises acetone and an alkoxylated lanolin oil is disclosed. The method comprises applying the composition to a cured nail gel and allowing the composition to soak.

11 Claims, No Drawings

METHOD AND COMPOSITION FOR REMOVING RADIATION-CURABLE, PIGMENTED, ARTIFICIAL NAIL GEL COATINGS

CROSS REFERENCE TO RELATED APPLICATIONS

This application is a divisional of application Ser. No. 13/434,408, filed Mar. 29, 2012, granted as U.S. Pat. No. 8,697,619 on Apr. 15, 2014. Benefit of the filing date of said application is claimed.

BACKGROUND OF THE INVENTION

This invention relates to the field of radiation-curable gels useful for cosmetic adornment of natural nails. More particularly this invention relates to methods and compositions for removing radiation cured nail gels.

The use of radiation-curable gels in formation of nail enhancements or artificial nails has been an important part of the cosmetic industry since it was first introduced. U.S. Pat. No. 4,682,612, describing the use of actinic radiation-curable compositions suitable for preparation of artificial nails, is representative of this technology.

Ultra-violet radiation (UV) is the most conventional form of radiation used to cure gels in this art, however, visible light curing systems are also known. Professional nail technicians most typically apply UV curable gels designed for sculpting nails. Such UV-curable gels are usually composed of acrylic or methacrylic monomers and oligomers in a gel-like state that requires curing under a UV lamp. Such nail finishes can be applied directly to natural fingernails or toenails, or alternatively can be applied to nail extensions bonded to fingernails. In many cases, the artificial nails are coated with conventional nail polish after they are cured.

In addition, a considerable advantage of the use of the UV nail gel for the customer and the person performing the application is the reduced time needed to harden. A customer can spend up to an hour waiting for the solvent in nail enamel to evaporate, while the gel is set in 3 minutes or less. Disadvantageously, due to the crosslinked polymer which is formed while curing these gels they are much more difficult to remove than normal nail polishes. Thus, there is a need for compositions that give improved soak off capabilities.

This object, and others which will become apparent from the following disclosure are achieved by the present invention which comprises in one aspect a composition comprising acetone and a derivatized lanolin, namely alkoxylated lanolin oil.

In another aspect the invention comprises a method comprising applying the composition of the invention to radiation cured nail gel, allowing the composition to soak for a period of time, and then removing the cured nail gel.

In some embodiments the lanolin oil is ethoxylated and propoxylated. The invention also comprises including about 2 to 3% by weight of the alkoxylated lanolin oil in the composition, the balance being primarily acetone and optionally other solvents known in the art, emollients, and dyes.

DETAILED DESCRIPTION OF PREFERRED EMBODIMENTS

By the term "nail gel," we mean a radiation-curable composition comprising photoinitiator, ethylenically unsaturated monomers and/or oligomers, having a viscosity suitable for coating natural or artificial nails, or artificial nails and extensions, as well as adorning such nails.

There are many possible embodiments of the nail gel. In some embodiments the gel is comprised of 50-70% by weight of an aliphatic polyester based urethane multimethacrylate oligomer, 15-25% by weight 2-hydroxyethyl methacrylate (HEMA), 15-25% by weight 2-hydroxypropyl methacrylate (HPMA), 1-5% (photoinitiator) and 0.1-10% by weight of a thixotropic additive, and 0.1-10% by weight FD&C Red #7 Calcium Lake pigment. Other embodiments can be comprised of aliphatic polyester based urethane diacrylate oligomer and FD&C Red #6 lake pigment.

The cured nail gel removal composition of the invention comprises acetone, optional conventional additives including other solvents, and a derivatized lanolin which is an alkoxylated lanolin oil. Suitable amounts of alkoxylated lanolin oil are between 1 and 5% but more preferably about 2 to 3%. We have observed soaking time is optimized at around 2.5% of many embodiments.

UV-curable artificial nail gels can be comprised of a wide variety of compounds containing one or more radical polymerizable unsaturated double bonds. Typical examples include esters and amides of acrylic and methacrylic acid. The esters of acrylic and methacrylic acid are herein termed (meth)acrylic ester. Specific but not limiting examples of mono methyl (meth)acrylic esters include: methyl (meth)acrylate, ethyl (meth)acrylate hydroxypropyl (meth)acrylate, ethyl (meth)acrylate, butyl (meth)acrylate, hydroxy ethyl (meth)acrylate, butoxyethyl (meth)acrylate, diethylaminoethyl (meth)acrylate, 2-ethylhexyl (meth)acrylate, ethoxyethyl (meth)acrylate, t-butyl aminoethyl (meth)acrylate, methoxyethylene glycol (meth)acrylate, phosphoethyl (meth)acrylate, methoxy propyl (meth)acrylate, methoxy polyethylene glycol(meth)acrylate, phenoxyethylene glycol (meth)acrylate, phenoxypolyethylene glycol (meth)acrylate, 2-hydroxy-3-phenoxypropyl (meth)acrylate, 2-(meth)acryloxyethylsuccinic acid, 2-(meth)acryloylethylphthalic acid, 2-(meth)acryloyloxypropylphthalic acid, stearyl (meth)acrylate, isobornyl (meth)acrylate, 3-chloro-2-hydroxypropyl (meth)acrylate, tetrahydrofurfuryl (meth)acrylate, (meth)acrylamides and allyl monomers. Specific but not limiting examples of difunctional methacryl esters include: 1,4-butane diol di(meth)acrylate, 1,6-hexanediol di(meth)acrylate, 1,9-nonanediol di(meth)acrylate, 1,10-decanediol di(meth)acrylate, neopentyl glycol di(meth)acrylate, 2-methyl-1,8-octane diol di(meth)acrylate, glycerol di(meth)acrylate, ethylene glycol di(meth)acrylate, triethylene glycol di(meth)acrylate, polyethylene glycol di(meth)acrylate, polypropylene glycol di(meth)acrylate, ethoxylated propylene glycol di(meth)acrylate, ethoxylated polypropylene glycol di(meth)acrylate, polyethoxypropoxy di(meth)acrylate, ethoxylated bisphenol A di(meth)acrylate, propoxylated bisphenol A di(meth)acrylate, propoxylated ethoxylated bisphenol A di(meth)acrylate, bisphenol-A glycidyl methacrylate, tricyclodecanedimethanol di(meth)acrylates glycerin di(meth)acrylate, ethoxylated glycerin di(meth)acrylate, bis acrylamides, bis allyl ethers and allyl (meth)acrylates. Examples of tri and or higher (meth)acryloyl esters include trimethylol propane tri(meth)acrylate, ethoxylated glycerin tri(meth)acrylate, ethoxylated trimethylolpropane tri(meth)acrylate, ditrimethylol propane tetra(meth)acrylate, pentaerythritol tri(meth)acrylate, pentaerythritol tetra(meth)acrylate, propoxylated pentaerythritol tetra(meth)acrylate, ethoxylated pentaerythritol tetra(meth)acrylate, dipentaerythritol penta(meth)acrylate, dipentaerythritol hexa(meth)acrylate, and ethoxlated iscyanuric acid tri(meth)acrylates.

Urethane(meth)acrylates having at least two or more acryl or methacryl groups and a urethane group can also be used. Examples include: urethanes based on aliphatic, aromatic, polyester, and polyether polyols and aliphatic, aromatic, polyester, and polyether diisocyanates capped with (meth) acrylate end-groups. Isocyanate prepolymers can also be used in place of the polyol-diisocyanate core. Epoxy (meth)acrylates and epoxy urethane (meth)acrylates, useful in the present invention, have at least two or more acryl or methacryl groups and, optionally, a urethane group. Examples include epoxy (meth)acrylates based on aliphatic or aromatic epoxy prepolymers capped with (meth)acrylate end-groups. A aliphatic or aromatic urethane spacer can be optionally inserted between the epoxy and the (meth)acrylate endgroup(s). Acrylated polyester oligomers, useful in the present invention, have at least two or more acryl or methacryl groups and a polyester core. Acrylated polyether oligomers, useful in the present invention, have at least two or more acryl or methacryl groups and a polyether core. Acrylated acrylate oligomers, useful in the present invention, have at least two or more acryl or methacryl groups and a polyacrylic core. These reactive urethanes, epoxies, polyesters, polyethers and acrylics are available from several suppliers including BASF Corporation, Bayer MaterialScience, Bomar Specialties Co, Cognis Corporation, Cytec Industries Inc, DSM NeoResins, Eternal Chemical Co, Ltd, IGM Resins, Rahn AG, Sartomer USA, LLC, and SI Group, Inc.

In addition to the above-described (meth)acrylate-based polymerizable monomers, other polymerizable monomers, oligomers or polymers of monomers which contain at least one free radical polymerizable group in the molecule may be used without any limitations in the curable gel. These monomers may contain other groups such as carboxyl groups to improve adhesion.

A compound having at least one free radical polymerizable group includes not only a single component but also a mixture of polymerizable monomers. Thus, combinations of two or more materials containing free radical polymerizable groups may be used in combination.

The gels also contain a photoinitiator. Examples of these include: benzyl ketones, monomeric hydroxyl ketones, polymeric hydroxyl ketones, alpha -amino ketones, acyl phosphine oxides, metallocenes, benzophenone, benzophenone derivatives, and the like. Specific examples include: 1-hydroxy-cyclohexylphenylketone, benzophenone, 2-benzyl-2-(dimethylamino)-1-(4-(4-morphorlinyl)phenyl)-1-butanone, 2-methyl-1-(4-methylthio)phenyl-2-(4-morphorlinyl)-1-propanone, diphenyl-(2,4,6-trimethylbenzoyl) phosphine oxide, phenyl bis(2,4,6-trimethylbenzoyl) phosphine oxide, benzyl-dimethylketal, isopropylthioxanthone, and mixtures thereof.

Photo accelerators such as aliphatic or aromatic amines may also be included in the gel as well as fillers, inhibitors, plasticizers, polymers, and adhesion promoters.

Gels with or without pigment can be used.

Suitable pigments which can be incorporated into the gels include barium, calcium and aluminum lakes, iron oxides, chromates, molybdates, cadmiums, metallic or mixed metallic oxides, talcs, carmine, titanium dioxide, chromium hydroxides, ferric ferrocyanide, ultramarines, titanium dioxide coated mica platelets, and/or bismuth oxychlorides, Preferred pigments include D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4., D&C Red No. 6, D&C Red No. 7, D&C Red No. 17, D&C Red No. 21, D&C Red No. 22, D&C Red No. 27, D&C Red No. 28, D&C Red No. 30. D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, as well as others listed on the FDA color additives website, and Annex IV of the Cosmetic Directive 76/768/EEC, Coloring Agents Permitted in Cosmetics as of Mar. 1, 2010.

EXAMPLES

Example 1

A nail gel removal composition was prepared with the following components and amounts.

TABLE 1

| Material | % by weight |
| --- | --- |
| Violet #1 Dye Powder | 0.0012 |
| Violet #2 Dye Solution | 0.0621 |
| Alkoxylated lanolin oil (Ritalan Aws brand) | 2.5694 |
| Acetone | 97.3673 |

Swell time in seconds was measured for compositions having varying amounts of alkoxylated lanolin oil and the results were as follows:

| UV Curable Gel | Solvent | Swell Time | Std Deviation |
| --- | --- | --- | --- |
| Gelinium Gloss[1] | 100% Acetone | 481 | 45 |
| Gelinium Gloss[1] | 2.5% Lanolin in Acetone | 383 | 16 |
| Gelinium Gloss[1] | 5% Lanolin in Acetone | 408 | 26 |
| Gelinium Clear[1] | 100% Acetone | 222 | 12 |
| Gelinium Clear | 1.25% Lanolin in Acetone | 190 | 10 |
| Gelinium Clear[1] | 2.5% Lanolin in Acetone | 168 | 14 |
| Gelinium Clear[1] | 3.75% Lanolin in Acetone | 226 | 56 |
| Gelinium Clear[1] | 5% Lanolin in Acetone | 230 | 28 |

[1]Available From Amazing Products NV/SA, Boomgardreef 9, B-2900 Schoten, Belgium.

Lower swell time indicates better efficiency for removing UV cured nail gel.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A method of removing UV-cured nail gel from a coated human nail comprising applying a composition comprising an alkoxylated lanolin oil and at least one solvent comprising acetone to the cured nail gel and allowing the composition to soak into the cured nail gel for a period of time until the cured nail gel becomes removable wherein the acetone comprises from 95% to 98.75% by weight of the composition.

2. The method of claim 1 wherein the at least one solvent is further comprises ethyl acetate.

3. The method of claim 1 wherein the alkoxylated lanolin oil comprises about 2% to 3% by weight of the composition.

4. The method of claim 1 wherein the alkoxylated lanolin oil is an ethoxylated/propoxylated lanolin oil.

5. The method of claim 1 wherein the alkoxylated lanolin oil is PPG-12-PEG-65 lanolin oil wherein PPG is polypropylene glycol and PEG is polyethylene glycol.

6. The method of claim 1 wherein the alkoxylated lanolin oil comprises 1.25% to 5% by weight of the composition.

7. The method of claim 1 wherein the solvent consists of acetone.

8. The method of claim 1 wherein the solvent consists of acetone and the alkoxylated lanolin oil comprises 1.25% to 5% by weight of the composition.

9. The method of claim 8 wherein the alkoxylated lanolin oil is PPG-12-PEG-65 lanolin oil wherein PPG is polypropylene glycol and PEG is polyethylene glycol.

10. The method of claim 8 wherein the alkoxylated lanolin oil is an ethoxylated/propoxylated lanolin oil.

11. The method of claim 1 wherein the composition is allowed to soak into the nail gel a period of time ranging from 168 seconds to for less than 481 seconds until the nail gel becomes removable.

* * * * *